(12) United States Patent
Mueller

(10) Patent No.: US 6,952,946 B2
(45) Date of Patent: Oct. 11, 2005

(54) METHOD FOR THE GAS CHROMATOGRAPHIC ANALYSIS OF A SAMPLE, AND ANALYZER

(75) Inventor: Friedhelm Mueller, Linkenheim-Hochstetten (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/636,782

(22) Filed: Aug. 8, 2003

(65) Prior Publication Data

US 2004/0099046 A1 May 27, 2004

Related U.S. Application Data

(63) Continuation of application No. PCT/DE02/00434, filed on Feb. 6, 2002.

(30) Foreign Application Priority Data

Feb. 8, 2001 (DE) .......................................... 101 05 728

(51) Int. Cl.$^7$ ............................................... G01N 30/02
(52) U.S. Cl. .................................................. 73/23.4
(58) Field of Search .............................. 73/23.35, 23.36, 73/23.37, 23.38, 23.39, 23.4, 23.41, 23.42, 25.01, 25.02, 25.03, 25.04, 25.05

(56) References Cited

U.S. PATENT DOCUMENTS

| | | | | |
|---|---|---|---|---|
| 2,633,737 A | * | 4/1953 | Richardson | ................ 73/25.03 |
| 2,935,867 A | * | 5/1960 | Christensen | ................ 73/25.05 |
| 3,097,518 A | * | 7/1963 | Taylor et al. | ................. 73/23.4 |
| 3,395,567 A | * | 8/1968 | Sanga et al. | ................... 73/23.4 |
| 3,408,854 A | * | 11/1968 | Larson | ........................ 73/23.4 |
| 3,562,501 A | * | 2/1971 | Mears | .......................... 702/32 |
| 3,592,043 A | * | 7/1971 | Munk | ........................ 73/61.58 |
| 3,686,923 A | | 8/1972 | Favre | |
| 3,847,546 A | * | 11/1974 | Paul | ............................ 436/157 |
| 4,215,563 A | | 8/1980 | Clardy et al. | |
| 4,215,564 A | * | 8/1980 | Lawson et al. | ............. 73/25.04 |
| 4,226,112 A | * | 10/1980 | Jibelian | ...................... 73/23.35 |
| 6,447,581 B2 | | 9/2002 | Gellert et al. | |
| 2001/0029772 A1 | | 10/2001 | Dieter et al. | |

FOREIGN PATENT DOCUMENTS

| | | | |
|---|---|---|---|
| DE | 38 31 548 C2 | 3/1989 | |
| JP | 61-212759 A | 9/1986 | |
| JP | 82-01368 A | 8/1996 | |
| JP | 411337542 A | * 12/1999 | ........... G01N/30/60 |
| WO | WO 00/17634 A2 | 3/2000 | |

OTHER PUBLICATIONS

Douglas A. Skook and James J. Leary, "Principles of Instrumental Analysis", 4th Ed., Saunders College Publishing, 1992 (cover, title page and pp. 607, 611 and 612 only).*
U.S. Appl. No. 07/098,573, Stephens et al.

* cited by examiner

*Primary Examiner*—Charles Garber
(74) *Attorney, Agent, or Firm*—Sughrue Mion, PLLC

(57) ABSTRACT

In a gas chromatograph, an injected sample for analysis (3) is passed through a separation device (5) to separate components present in the sample; at the end of the separation device, selected components are detected by a detector (12) and determined quantitatively on the basis of the detector signal (13) supplied by the detector. To permit validation and also to increase the accuracy of the analysis, the sample (3) is determined nondestructively by an additional detector (16) upstream from the separation device (5) and is determined quantitatively on the basis of the additional detector signal (17) supplied by the additional detector (16). The result of the quantitative determination of the sample (3) is used to verify the analysis.

6 Claims, 4 Drawing Sheets

28 = Detector Circuit

28 = Detector Circuit

METHOD FOR THE GAS CHROMATOGRAPHIC ANALYSIS OF A SAMPLE, AND ANALYZER

This is a Continuation of International Application PCT/DE02/00434, with an international filing date of Feb. 6, 2002, which was published under PCT Article 21(2) in German, and the disclosure of which is incorporated into this application by reference.

FIELD OF AND BACKGROUND OF THE INVENTION

The present invention relates to analysis methods using gas chromatography and to associated analyzing devices.

In gas chromatography, a dosing device injects a mixture of substances to be analyzed (a sample) in the form of the shortest possible, sharply delineated sample slug at the inlet of a separation device (e.g. a separation column or a system of separation columns). The sample is then transported through the separation device by a carrier gas stream. Individual components of the sample interact in different ways with a separation substance in the separation device, so they are transported through the separation device at different rates and appear in succession at the outlet. Thus, different successive zones containing the separated components of the sample are formed from the single mixed zone of the initial sample slug. The width of these zones is greater than that of the sample slug because of the transport of the components through the separation device and their interaction with the separation substance. At the outlet of the separation device, the separated components of the sample are detected by a detector, which generates an analog detector signal (chromatogram) having peaks for each individual component separated. The width of each individual peak corresponds to the width of the zone of the respective component, while the height of the peak depends on the concentration of that component in the carrier gas. The time integral over each peak, i.e., the peak area, is proportional to the quantity of the respective sample component, and thus to the quantity of sample dosed, and to the concentration of the respective component in the substance mixture for analysis. Therefore, to be able to determine the quantities of individual sample components and/or their concentrations from the peak areas, the peak areas must be multiplied by calibration factors (response factors), which must be determined in advance by calibration measurements for each component on the basis of calibration samples having a predetermined quantity and composition.

Therefore, for accurate and reliable gas chromatographic analysis of a sample, the sample must be injected with a suitable precision and reliability. By calibrating the chromatograph at certain intervals, it is possible to detect changes in the chromatograph since the last calibration. If substantial changes have occurred, it must be feared that the analytical results obtained since the last calibration might have been faulty and might have resulted in faulty process control, for example. In such cases, the calibration cycles can be shortened. Starting at the time of each new calibration, analytical results provided by that chromatograph are assumed to be correct until the next calibration.

However, validation of analytical results, i.e., confirmation of the accuracy of each individual analysis, is being required today to an increasing extent, but this cannot be accomplished through calibration alone, as shown above.

One possible method of validation is the so-called internal standardization method (100% method) in which a sample is analyzed completely quantitatively, and then the total quantity of sample is calculated from the sum of all component quantities determined from the peak areas. If the total calculated quantity of sample fluctuates in successive analyses, the areas of the peaks to be determined are corrected accordingly. However, the prerequisites for this include complete analysis of a sample, using only a single detector (because two or more detectors may vary to different extents) and constancy of the response factors of all components of the sample. However, these prerequisites are not usually met. Thus, in process chromatography in particular, components not of interest are usually cut out or backflushed at cutting points within the separation system, but detectors are not present at all outlets of the separation system.

Another possible method of validating analytical results is the internal standard method, in which a known amount of a standard compound is added to the sample. The areas of the peaks to be determined are corrected to the extent to which the peak area of the standard peak fluctuates in successive analyses. However, although this method is used in laboratory chromatography, it cannot be used in process chromatography in general, because accurate addition of a standard to a sample taken online from a process creates more problems than it eliminates.

OBJECTS OF THE INVENTION

Therefore, one object of the present invention is to permit validation of analysis results in gas chromatography. Another object is to increase the accuracy of the analysis results, in particular in process gas chromatography.

SUMMARY OF THE INVENTION

According to one formulation of the invention, these and other objects are solved by a method of gas chromatographic analysis of a dosed sample that includes: passing the sample through a separation device and thereby separating components contained in the sample, detecting selected components of the sample at an end of the separation device with a detector and quantitatively determining the selected components in accordance with a detector signal supplied by the detector, detecting the sample nondestructively upstream from the separation device with an additional detector and quantitatively determining the sample in accordance with an additional detector signal supplied by the additional detector, and verifying the analysis with the quantitative determination of the sample.

Building upon a conventional method of gas chromatographic analysis of a dosed sample, which is passed through a separation device to separate the components present in the sample, selected components being detected by a detector and determined quantitatively at the end of this device on the basis of the detector signal supplied by the detector, the present invention detects the sample nondestructively by using an additional detector upstream from the separation device, quantitatively determining the sample on the basis of the additional detector signal supplied by the additional detector, and using the result of the quantitative determination of the sample to verify the analysis.

The detector signal supplied by the additional detector represents an actual value for the quantity of sample actually introduced into the separation device, so that validation results are possible using this actual value. The sample must not be destroyed by this additional detection, so suitable examples of the additional detector would include thermal conductivity detectors, various optical detectors, or detectors that operate with acoustic surface waves, but would not include, e.g., flame ionization detectors. The separation device is understood to be a single separation column or a complete system of separation columns or an individual column as a component of a system of separation columns, where the separation device may also have multiple outputs with detectors accordingly. Quantitative detection of the sample is thus not limited only to the site directly downstream from the dosing of the sample, but may also be performed wherever separation columns are linked together via switching devices for cutting out or branching off sample components or backflushing individual separation columns. Dosing errors and sample losses during switching can thus be detected and corrected.

Dosing of the sample is thus validated advantageously by the fact that the additional detector performs a quantitative determination on the sample immediately after the sample is dosed. The result of the quantitative determinations on the sample is then compared with the known value of a calibration sample quantity. To do so, a calibration sample slug is detected once with the additional detector and the theoretical area of the additional detector signal thereby obtained is stored. Then the actual area of the additional detector signal generated in detection of a sample slug is compared with this theoretical area in each case. Depending on the current composition of a sample to be analyzed, it and the actual area obtained with it will deviate from the corresponding calibration sample. However, if these deviations are minor, for example, and at the same time major deviations in the sample composition are detected by the detector at the end of the separation device, then it is certain that the major changes detected at the end of the separation device are in fact representative of changes in the sample composition and are not caused by dosing errors. Major and/or sudden changes in a process from which the sample for analysis is obtained can thus be detected with certainty, so it is possible to intervene in the process subsequently with countermeasures.

As mentioned above, in complete analysis of a sample, the sample quantity can also be determined from the sum of all peak areas of the chromatogram using the 100% method. In this case, the additional detector offers the advantage of monitoring the functionality of the detector at the outlet of the separation device and/or that of detectors at multiple outlets. For example, if the sensitivity of a detector varies over time, different results will be obtained in determination of sample quantity by the 100% method and the additional detector signal of the additional detector.

Malfunctioning of switching devices between individual separation columns can also be detected in the same way as described for sample dosing at the inlet of the separation device.

Furthermore, the accuracy of the chromatographic analysis can be increased by correcting the results of quantitative determination of selected components of the sample by the results of quantitative determination of the sample. As explained in the beginning, for quantitative determination of selected components of the sample, the respective peak areas in the detector signal are multiplied by calibration factors (response factors) determined previously for these components on the basis of calibration samples having a predetermined quantity and composition. An actual dosing of sample which deviates from the theoretical dosing quantity can therefore be taken out of the result of the quantitative determination of the components by calculation using the substance-specific components of the calibration factors, e.g., the thermal conductivity of the sample components.

As mentioned above, the additional detectors must not destroy the sample before it enters the separation device. In order not to impair overall separation performance, the measurement path of the additional detector through which the sample flows preferably has cross-sectional dimensions corresponding at least approximately to the internal cross-sectional dimensions of the separation device. This prevents the sample slug, which is as short and as well-defined as possible, from being destroyed by the additional detector. The same thing is also true of the more or less separate zones of the sample components when the additional detector is situated between two separation columns of a system of separation columns.

BRIEF DESCRIPTION OF THE DRAWINGS

To further illustrate this invention, reference is made below to the figures of the drawing, which show in detail.

DETAILED DESCRIPTION OF THE PREFERRED EMBODIMENTS

Figure 1:
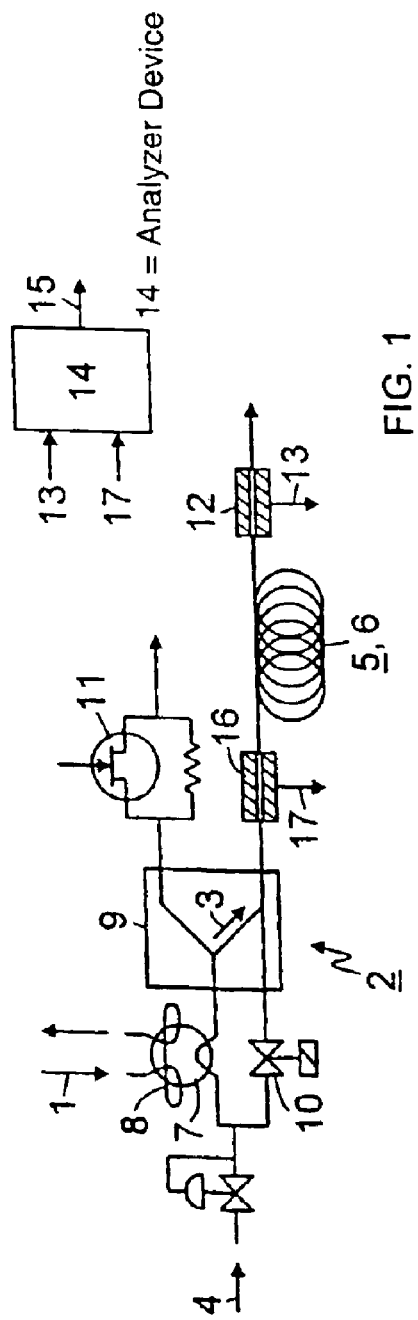
FIG. 1 an exemplary embodiment of a gas chromatograph that operates by the method according to this invention, having one detector at the end of the separation column and another detector at the beginning of the separation column.

FIG. 1 shows a gas chromatograph for analysis of a sample (substance mixture) 1, which is sent to a dosing device 2, such as that already known from patent publication WO 00/17634, after being sampled from an industrial process and worked up, e.g., by evaporation. The dosing device 2 is used to introduce a predetermined dosage quantity of the sample 1 in the form of a short and sharply delineated sample slug 3 into a carrier gas stream 4 at a predetermined point in time and to supply it to a separation device 5, here in the form of a single separation column 6. Therefore, the dosing device 2 has a dosing valve 7, which in a first switch position shown here introduces the sample 1 into a dosing volume 8. In a second switch position, reached by a 60° rotation, the dosing volume 8 is switched to the path for the carrier gas 4 and is sent by the carrier gas 4 to an injector 9. As long as a solenoid valve 10 is open, the carrier gas 4 flows through the solenoid valve 10 and the injector 9 into the separation column 6, while the sample 1 is diverted to the outside from the dosing volume 8 through a diaphragm valve 11, which is used for adjusting the injector 9. If the solenoid valve 10 is closed for a predetermined period of time, a portion of the sample is diverted then within the injector 9 from the sample 1 and is introduced as a sharply delimited sample slug 3 into the separation column 6. The separation column 6 is designed to separate the sample components contained in the sample slug 3 as they flow through the separation column 6, so that the individual sample components arrive in succession at a detector 12 at the end of the separation column 6, where they are detected. The detector 12 supplies a detector signal 13, which is analyzed in an analyzer device 14 for quantitative determination of selected sample components. The analytical result 15 thus obtained can be sent to a process control and/or regulating device which can intervene in the process from which the sample 1 has been taken to control and/or regulate it as a function of the result 15.

To validate the analytical result 15, and in accordance with the invention, an additional detector 16 is installed between the dosing device 2 and the separation device 5 to detect the sample slug 3 nondestructively. The additional detector 16 supplies an additional detector signal 17, from which the sample quantity actually introduced into the separation column 5 is determined in the analyzer device 14.

Figure 2:
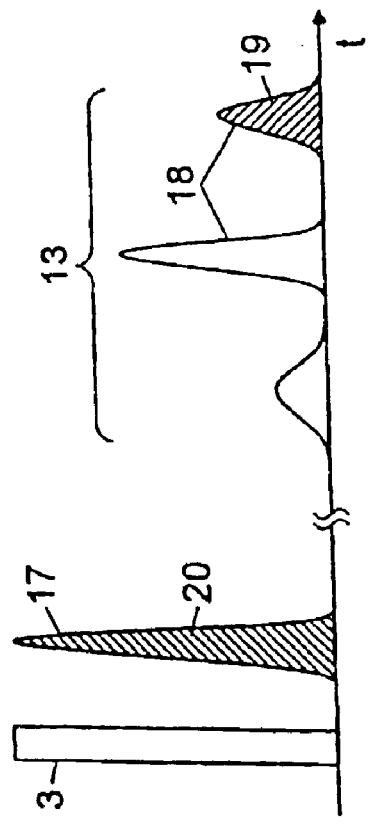
FIG. 2 an example of the detector signals supplied by the detector and the additional detector.

FIG. 2 shows, in chronological order, the sample slug 3 dispensed by the injector 9, the additional detector signal 17 supplied by the additional detector 16 and the detector signal 13 supplied by the detector 12. The detector signal 13 has a peak 18, for example, for each sample component detected, the peak area 19 being proportional to the quantity of the respective sample component. By multiplying the peak area 19 times a calibration factor determined in advance on the basis of a calibration sample having a known composition and quantity, the quantity of the respective peak component is calculated, assuming that the sample quantity charged to the separation device 5 corresponds precisely to the calibration sample quantity and/or is known precisely. Because of dosing errors, e.g., as a result of gradual changes in the dosing device 2, however, deviations may occur between the theoretical dosing quantity and the actual dosing quantity of the sample slug 3. The area 20 of the additional detector signal 17 supplied by the additional detector 16 is proportional to the actual dosing quantity and therefore permits a verification of the dosing up to a determination of the actual dosing quantity in each analytical procedure. To do so, for example, a calibration sample slug is detected once with the additional detector 16, and the theoretical area of the resulting additional detector signal 17 is stored. Then the actual area 20 of the additional detector signal 17 generated on detection of a sample slug 3 is compared each time with this theoretical area. By taking into account the calibration factors, the analytical result 15 can be corrected for each sample component by using the resulting deviation between the theoretical area and the actual area 20.

Figure 3:
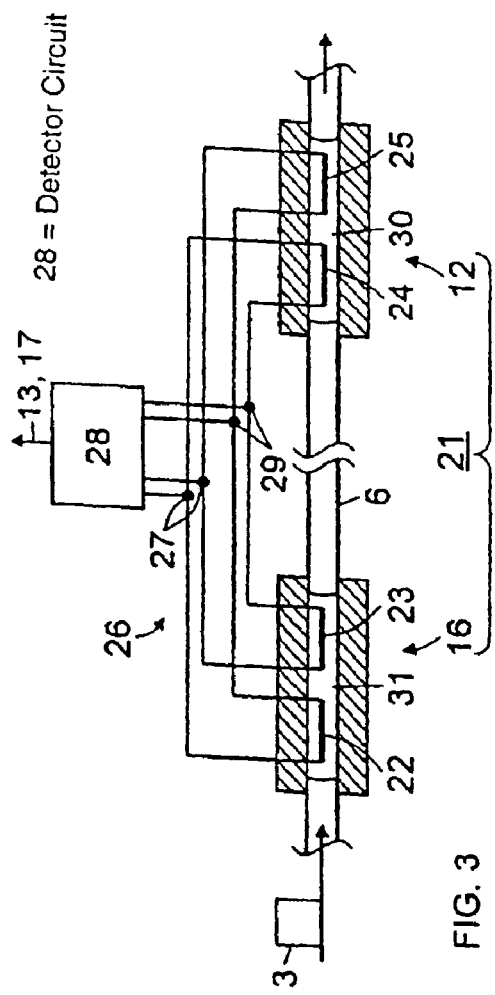
FIG. 3 an exemplary embodiment of the detector and additional detector.

FIG. 3 shows a thermal conductivity detector 21, which operates alternately as the detector 12 and as the additional detector 16. The thermal conductivity detector 21 has four heating resistors 22, 23, 24 and 25 in the form of wires arranged in a bridge circuit 26. The bridge circuit 26 is supplied with an electric current at two opposite circuit points 27 from a detector circuit 28, and the voltage occurring between the two other opposed circuit points 29 is detected by the detector circuit 28 to generate the detector signal 13 and/or the additional detector signal 17. The diagonally opposed heating resistors 24 and 25 in the bridge circuit 26 are situated at the end of the separation column 6 in a measurement path 30 of the detector 12, while the other two heating resistors 22 and 23 are arranged in an additional measurement path 31 of the additional detector 16 connected between the dosing unit 2 (FIG. 1) and the separation column 6.

The measurement paths 30 and 31, but in particular the additional measurement path 31, are designed so that their internal cross-sectional dimensions correspond to those of the separation column 6, so that the shortest possible and most sharply delimited sample slug 3 is not disturbed by the additional detector 16, and the zones with the separated sample components appearing at the end of the separation column are not disturbed by the detector 12. The dosing slug 3 introduced by means of the carrier gas 4 into the separation column 6 first goes into the measurement path 31 of the additional detector 16, while the carrier gas 4 flows through the measurement path 30 of the detector 12. The thermal conductivity detector 21 then functions as the additional detector 16, with the measurement path 30 of the detector 12 serving as a reference path. Finally, when the separated sample components enter the measurement path 30 of the detector 12, the thermal conductivity detector 21 operates as the detector 12, with the measurement path 31 of the additional detector 16 through which the carrier gas 4 flows serving as the reference path for the detector 12. The heating resistors 22, 23, 24 and 25 and the inside walls of the measurement paths 30 and 31 are made of materials that are inert with respect to the substance mixture to be analyzed and/or the carrier gas 4, i.e., the walls are made of gold and/or silicon dioxide (quartz), for example, to prevent any change in the substance mixture due to chemical reactions.

Figure 4:
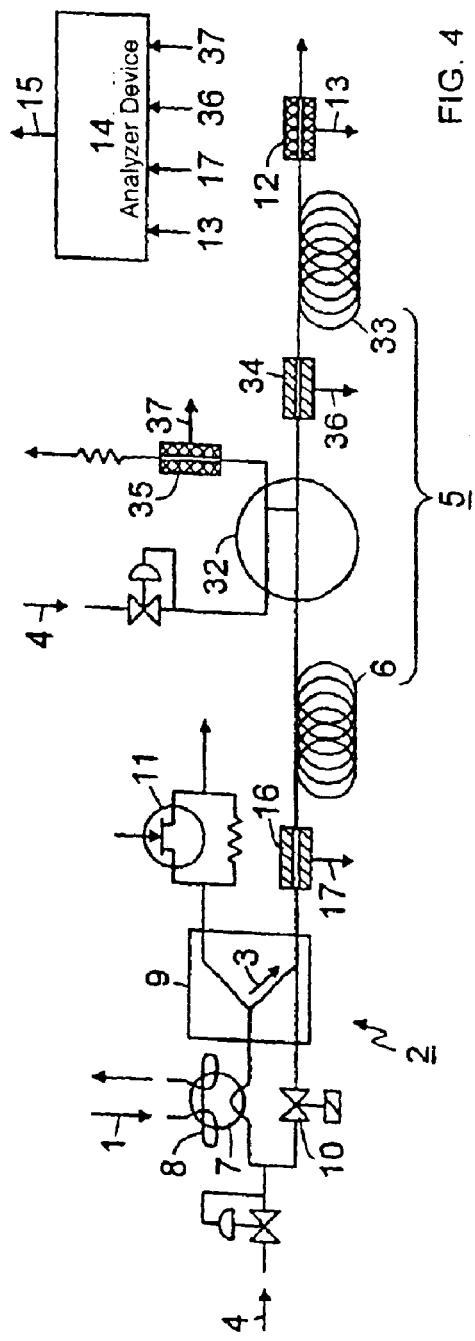
FIG. 4 an exemplary embodiment of a gas chromatograph having two separation columns connected in series and a switching device between them for backflushing the first separation column.

The gas chromatograph shown in FIG. 4 differs from that in FIG. 1 in that the separation column 6 of the separation device 5 functions as a precolumn having a main column 33 connected downstream via a switching device 32. The switching device 32 has the function of backflushing the precolumn 6 with carrier gas 4 when the sample slug 3 has left it and has entered the main column 33 with the partially separated sample components. The detector 12 is situated at the end of the main column 33, where it detects the completely separated sample components. In addition to the additional detector 16 at the inlet of the precolumn 6, additional detectors 34 and 35 are also situated at the outlets of the switching device 32, with the additional detector 34 being situated between the switching device 32 and the inlet of the main column 33. The area of the detector signal 36 supplied by the additional detector 34 is thus proportional to the quantity of sample actually reaching the main column 33, while the area of the detector signal 37 supplied by the additional detector 35 is proportional to the-sample quantities leaving the chromatograph there. By analyzing the detector signals 13, 17, 36 and 37 in the analyzer device 14, it is thus possible to determine precisely which quantities of sample have in fact entered the separation columns 6 and 33, so that malfunctioning of the dosing device 2 and the switching device 32 can be detected and the effects thereof on the analytical results 15 can be taken into account and/or corrected, as explained above with reference to FIGS. 1 through 3. As shown by the different hatched areas in the figures, the functions of two detectors 16 and 34 and/or 12 and 37 are performed in this embodiment by a single thermal conductivity detector. The detectors 16 and 34, which are, e.g., implemented by a thermal conductivity detector, are selected with regard to the functioning of the chromatograph so that the sample is always flowing through only one of the two detectors, while the carrier gas 4 is flowing through the other detector at the same time.

Figure 5:
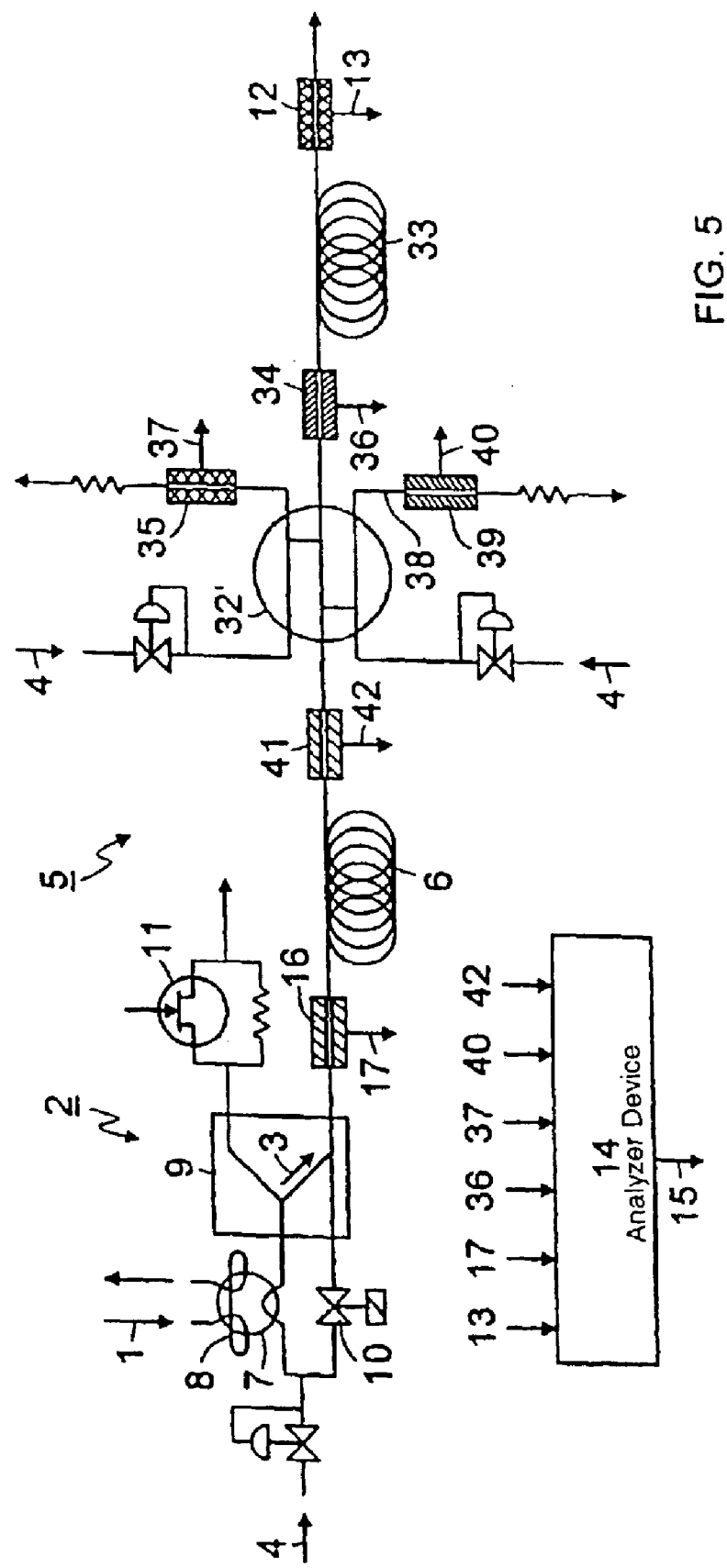
FIG. 5 an exemplary embodiment of a gas chromatograph having two separation columns connected in series and a switching device between them for cutting out sample components and backflushing the first separation column, and FIG. 6 an exemplary embodiment of a gas chromatograph having a switching device downstream from a first separation column for distributing the sample components between two additional separation columns and backflushing the first separation column.

In the case of the gas chromatograph shown in FIG. 5, in contrast with FIG. 4, the switching device 32' is designed to optionally remove (cut out) the preseparated sample components partially or entirely from the separation device 5 via a gas path after leaving the precolumn 6 and at the same time to flush the main column 33 with the carrier gas 4 or to convey the preseparated sample components further into the main column 33 and, if necessary, at the same time backflush the precolumn 6 with the carrier gas. Such a switching device 32' is known from the aforementioned publication WO 00/17634, for example. As in the example according to FIG. 4, detectors 34, 35 and 39 are provided at all the outlets of the switching device 32' to determine—by analyzing their detector signals 36, 37 and 40 together with the detector signals 13 and 17 of the detectors 12 and 13 at the beginning and end of the separation column 5—which sample quantities are in fact entering the separation columns 6 and 33 and/or leaving the switching device 32'. Quantitative analysis of sample components cut out by the switching device 32' is advantageously performed by a detector 41 directly at the end of the precolumn 6 and not by the detector 39, for example, so that the detector signal 42 is not influenced by the switching device 32'. Here again, the functions of two detectors, e.g., 12 and 35, are preferably performed by a single thermal conductivity detector.

Figure 6:
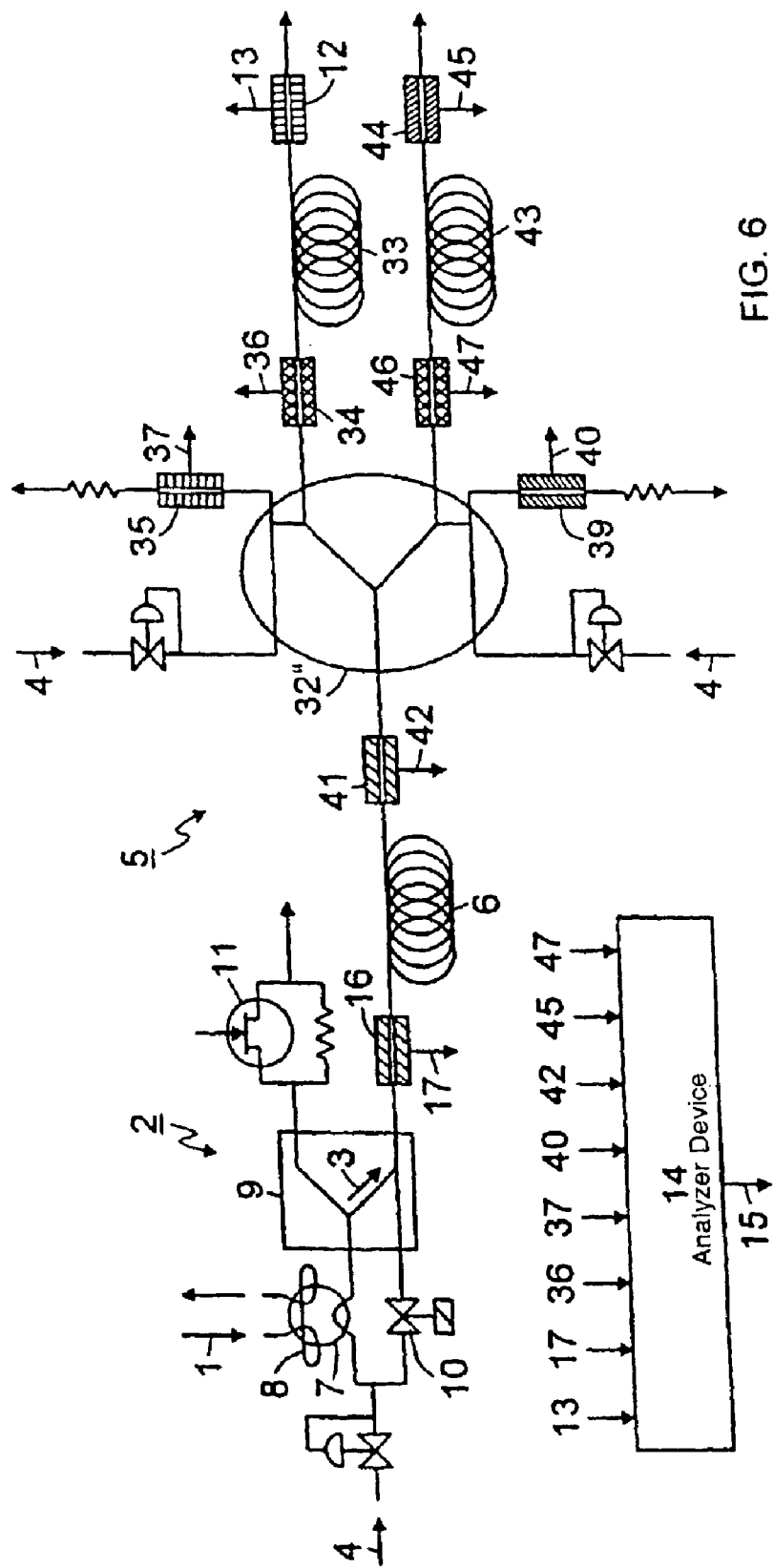

In the case of the gas chromatograph shown in FIG. 6, in contrast with that in FIG. 5, the switching device 32" is additionally designed to switch the sample between the main column 33 and another main column 43. A detector 44, provided at the outlet of the additional main column 43, generates a detector signal 45, and at the inlet of the additional main column 43 there is another detector 46, which generates a detector signal 47. Here again, by analysis of the detector signals 13, 17, 36, 37, 40, 42, 45 and 47, it is possible to ascertain which sample quantities are in fact entering the separation columns 6, 33 and 43 and/or leaving the switching device 32".

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. A method of gas chromatographic analysis of a dosed sample, comprising:
    passing the sample through a separation device and thereby separating components contained in the sample,
    detecting selected components of the sample at an end of the separation device with a detector and quantitatively determining the selected components in accordance with a detector signal supplied by the detector,
    detecting the sample nondestructively upstream from the separation device with an additional detector and quantitatively determining the sample in accordance with an additional detector signal supplied by the additional detector, and
    verifying the analysis with the quantitative determination of the samples,
    wherein the additional detector comprises a thermal conductivity detector, and
    wherein the thermal conductivity detector functions alternately as the detector and as the additional detector,
    the thermal conductivity detector includes a bridge circuit,
    two diagonally opposed heating resistors in the bridge circuit are situated in the two different bridge halves in a measurement path of the detector,
    two further heating resistors in the bridge circuit are situated in a measurement path of the additional detector, and
    the sample flows through only one of the two measurement paths at any given time.

2. The method as recited in claim 1, wherein the sample is determined quantitatively with the additional detector immediately after the sample is dosed, and
    wherein the quantitative determination of the sample is compared with a known value of a calibration sample quantity.

3. The method as recited in claim 1, further comprising:
    correcting a result of the quantitative determination of the selected components of the sample by the quantitative determination of the sample.

4. The method as recited in claim 1, wherein the additional detector has a measurement path, through which the sample flows, having a cross-section at least approximately equal to an internal cross-section of the separation device.

5. A gas chromatographic analyzer, comprising:
    a separation device, through which a dosed sample is passed, separating components contained in the sample,
    a detector detecting selected components at an end of the separation device and outputting a detector signal as a quantitative determination of the selected components,
    an additional detector detecting the sample nondestructively upstream from the separation device and outputting an additional detector signal as a quantitative determination of the sample, and
    an analyzer device verifying the analysis from the additional detector signal providing the quantitative determination of the sample,
    wherein the additional detector comprises a thermal conductivity detector,
    and wherein the thermal conductivity detector is configured to function alternately as the detector and as the additional detector,
    the thermal conductivity detector comprises a bridge circuit,
    two diagonally opposed heating resistors in the bridge circuit are situated in the two different bridge halves in a measurement oath of the detector,
    two further heating resistors in the bridge circuit are situated in a measurement path of the additional detector, and
    the analyzer is configured to pass the sample through only one of the two measurement paths at any given time.

6. The analyzer as recited in claim 5, wherein the additional detector has a measurement path, through which the sample flows, having a cross-section at least approximately equal to an internal cross-section of the separation device.

* * * * *